US010359337B1

(12) United States Patent
Bissel et al.

(10) Patent No.: US 10,359,337 B1
(45) Date of Patent: Jul. 23, 2019

(54) TEST SECTIONS, WIND TUNNELS INCLUDING THE SAME, AND METHODS OF USING THE SAME

(71) Applicant: WinField United, River Falls, WI (US)

(72) Inventors: Daniel Bissel, Eagan, MN (US); Lee Boles, River Falls, WI (US); Andrea Clark, River Falls, WI (US)

(73) Assignee: Winfield Solutions, LLC, Shoreview, MN (US)

( * ) Notice: Subject to any disclaimer, the term of this patent is extended or adjusted under 35 U.S.C. 154(b) by 0 days.

(21) Appl. No.: 16/198,349

(22) Filed: Nov. 21, 2018

(51) Int. Cl.
*G01M 9/04* (2006.01)
*B05B 12/00* (2018.01)
(Continued)

(52) U.S. Cl.
CPC ........... *G01M 9/04* (2013.01); *B05B 1/02* (2013.01); *B05B 1/12* (2013.01)

(58) Field of Classification Search
CPC .......... G01M 9/04; G01M 9/02; G01M 9/062; G01M 9/06; G01M 9/065; G01M 9/08; G01M 17/007; G01M 17/0074; G01M 9/067; G01M 10/00; G01M 15/14; G01M 17/0072; G01M 13/027; G01M 17/0076; B05B 1/20; B05B 1/30; B05B 12/12; B05B 7/0408; B05B 15/55; B05B 1/08; B05B 1/12; B05B 1/14; B05B 12/04; B05B 12/085; B05B 12/087; B05B 13/005; B05B 1/005; B05B 1/044; B05B 1/1636; B05B 1/185; B05B 1/24; B05B 1/34; B05B 12/006; B05B 12/008; B05B 12/08; B05B 12/081; B05B 12/082; B05B 12/126; B05B 15/62; B05B 1/1654; B05B 1/18; B05B 1/262; B05B 1/28; B05B 1/3006;
(Continued)

(56) References Cited

U.S. PATENT DOCUMENTS

| 3,994,438 A * | 11/1976 | Farmery | A01C 17/00 239/7 |
| 4,844,346 A * | 7/1989 | Coffey | A01M 7/0042 239/166 |

(Continued)

OTHER PUBLICATIONS

Ng, C.-L. et al. "Bag breakup of nonturbulent liquid jets in crossflow." International Journal of Multiphase Flow 34 (2008) pp. 241-259.

*Primary Examiner* — Andre J Allen
(74) *Attorney, Agent, or Firm* — Dorsey & Whitney LLP (57) ABSTRACT

In an embodiment, a test section comprises at least one surface defining an at least partially enclosed space. The at least partially enclosed space defines an airflow path for air to flow. The test section also comprises a nozzle disposed in the at least partially enclosed space. The nozzle is configured to spray an agricultural spray and is positioned to emit the agricultural spray such that at least a section of the agricultural spray exhibits a non-parallel angle relative to the airflow path defined by the at least partially enclosed space. The test section further comprises at least one stimulus source positioned to illuminate at least a portion of the agricultural spray adjacent to the nozzle. Additionally, the test section comprises at least one detector positioned to image at least the portion of the agricultural spray adjacent to the nozzle.

20 Claims, 7 Drawing Sheets

(51) Int. Cl.
*B05B 1/02* (2006.01)
*B05B 1/12* (2006.01)

(58) Field of Classification Search
CPC ......... B05B 1/3026; B05B 1/32; B05B 7/005; B05B 7/0093; B05B 7/0815; B05B 7/0846; B05B 7/1254; B05B 7/2416; B05B 7/2424; B05B 7/2489; B05B 7/262; B05B 9/002; B05B 9/007; B05B 9/04; B05B 9/0413; B05B 9/06; B05B 11/0005; B05B 12/00; B05B 12/002; B05B 12/004; B05B 12/02; B05B 12/06; B05B 12/084; B05B 12/10; B05B 12/122; B05B 12/124; B05B 12/1418; B05B 12/1472; B05B 12/149; B05B 12/16; B05B 12/18; B05B 13/0207; B05B 13/0235; B05B 13/04; B05B 14/00; B05B 15/00; B05B 15/52; B05B 15/525; B05B 15/555; B05B 15/65; B05B 15/70; B05B 17/0607; B05B 17/0646; B05B 1/00; B05B 1/02; B05B 1/04; B05B 1/046; B05B 1/048; B05B 1/083; B05B 1/086; B05B 1/16; B05B 1/1609; B05B 1/1645; B05B 1/1663; B05B 1/169; B05B 1/205; B05B 1/26; B05B 1/265; B05B 1/267; B05B 1/3013; B05B 1/3033; B05B 1/304; B05B 1/3046; B05B 1/306; B05B 1/3073; B05B 1/3086; B05B 1/326; B05B 1/3402; B05B 1/3405; B05B 3/04; B05B 3/0409; B05B 3/0486; B05B 3/1021; B05B 3/1035; B05B 3/1064; B05B 7/04; B05B 7/0416; B05B 7/062; B05B 7/08; B05B 7/0892; B05B 7/12; B05B 7/1209; B05B 7/1486; B05B 7/24; B05B 7/2464; B05B 7/2486; B05B 7/2497; B05B 9/01; B05B 9/0403; B05B 9/0406; B05B 9/0416; B05B 9/0423; B05B 9/0811; B05B 9/0838; B05B 9/085
USPC .............................. 73/147; 239/11; 504/204
See application file for complete search history.

(56) References Cited

U.S. PATENT DOCUMENTS

| | | | |
|---|---|---|---|
| 2004/0069875 A1* | 4/2004 | Bui | A01G 25/023 239/533.2 |
| 2006/0011741 A1* | 1/2006 | Hahn | A01M 7/0064 239/172 |
| 2015/0272106 A1* | 10/2015 | Schertz | A01M 7/0089 239/11 |
| 2016/0192642 A1* | 7/2016 | Lindner | A01N 57/20 504/204 |
| 2017/0036228 A1* | 2/2017 | Thurow | B05B 12/085 |
| 2018/0052088 A1* | 2/2018 | Sarkar | G01N 15/0227 |

* cited by examiner

```
                              ┌────────────────────────────────────────────────────────────┐
                              │ Flowing air along an airflow path of an at least partially │ ─ 505
                              │ enclosed space                                             │
                              └────────────────────────────────────────────────────────────┘
                                                        │
                                                        ▼
                              ┌────────────────────────────────────────────────────────────┐
                              │ Emitting an agricultural spray from a nozzle such that     │
                              │ at least a portion of the agricultural spray exhibits a    │ ─ 510
                              │ non-parallel angle relative to the air flowing along the   │
                              │ airflow path                                               │
                              └────────────────────────────────────────────────────────────┘
                                                        │
                                                        ▼
                              ┌────────────────────────────────────────────────────────────┐
                              │ Emitting a stimulus from at least one stimulus source to   │ ─ 515
                              │ illuminate at least a portion of the agricultural spray    │
                              │ that is adjacent to the nozzle                             │
                              └────────────────────────────────────────────────────────────┘
                                                        │
                                                        ▼
                              ┌────────────────────────────────────────────────────────────┐
                              │ Imaging at least the portion of the agricultural spray     │ ─ 520
                              │ that is adjacent to the nozzle with at least one detector  │
                              └────────────────────────────────────────────────────────────┘
```

TEST SECTIONS, WIND TUNNELS INCLUDING THE SAME, AND METHODS OF USING THE SAME

CROSS-REFERENCE TO RELATED APPLICATIONS

This application is filed concurrently with a patent application entitled Test Sections, "Methods of Using Drift Reduction Adjuvant Compositions" Ser. No. 16/198,384, which is herein incorporated by reference in its entirety for any useful purpose.

BACKGROUND

Due to increasing concern about pest control costs and environmental pollution associated with agricultural sprays, application of such sprays requires precision and care. Considerable research on spray drift has been conducted, but it remains a major problem associated with many agricultural spray applications.

Field tests provide some information on factors influencing spray drift. However, field tests are limited by weather conditions that may not be controlled and often vary during a test. Due to non-controlled environment, assessing the influence of some variables on spray drift is difficult. Laboratory tests are used to evaluate drift associated with spray deposits discharged from spray tips at various wind velocities in wind tunnels. However, wind tunnels are generally costly and may expose the tester to the agricultural spray, which may have negative health effects on the tester.

The US EPA will soon implement a new Drift Reduction Technology (DRT) program which would allow producers and other applicators to reduce the size of buffer zones required on some herbicide labels. DRT will need to be certified through spray particle analysis or field trials proving a reduction in fine droplets subject to off-target drift. More frequent use of wind tunnels may be required for certification.

SUMMARY

In an embodiment, a test section is disclosed. The test section comprises at least one surface defining an at least partially enclosed space. The at least partially enclosed space defines an airflow path for air to flow. The test section also comprises a nozzle disposed in the at least partially enclosed space. The nozzle is configured to spray an agricultural spray and is positioned to emit the agricultural spray such that at least a section of the agricultural spray exhibits a non-parallel angle relative to the airflow path defined by the at least partially enclosed space. The test section further comprises at least one stimulus source positioned to illuminate at least a portion of the agricultural spray adjacent to the nozzle. Additionally, the test section comprises at least one detector positioned to image at least the portion of the agricultural spray adjacent to the nozzle.

In an embodiment, a wind tunnel system is discloses. The wind tunnel comprises a test section. The test section comprises at least one surface defining an at least partially enclosed space. The at least partially enclosed space defines an airflow path for air to flow. The test section also comprises a nozzle disposed in the at least partially enclosed space. The nozzle is configured to spray an agricultural spray and is positioned to emit the agricultural spray such that at least a section of the agricultural spray exhibits a non-parallel angle relative to the airflow path defined by the at least partially enclosed space. The test section further comprises at least one stimulus source positioned to illuminate at least a portion of the agricultural spray adjacent to the nozzle. Additionally, the test section comprises at least one detector positioned to image at least the portion of the agricultural spray adjacent to the nozzle. The wind tunnel also comprises a blower configured to provide the air to the test region.

In an embodiment, a method is disclosed. The method comprises flowing air along an airflow path of an at least partially enclosed space. The at least partially enclosed space is defined by at least one surface. The method also comprises emitting an agricultural spray from a nozzle such that at least a section of the agricultural spray exhibits a non-parallel angle relative to the air flowing along the airflow path. The method further comprises emitting a stimulus from at least one stimulus source to illuminate at least a portion of the agricultural spray that is adjacent to the nozzle. The method additionally comprises imaging at least the portion of the agricultural spray that is adjacent to the nozzle with at least one detector.

In various implementations and alternatives, the at least one surface comprises a top surface, a bottom surface, and two lateral surfaces extending between the top surface and the bottom surface.

In various implementations and alternatives, the at least one surface comprises a first transparent section and a second transparent section, the at least one stimulus source is positioned to emit the stimulus into the at least partially enclosed space through the first transparent section, the at least one detector is positioned to image at least the portion of the agricultural spray that is adjacent to the nozzle through the second transparent section.

In various implementations and alternatives, the at least partially enclosed space is a completely enclosed space.

In various implementations and alternatives, the nozzle comprises a flat fan nozzle and an entirety of the agricultural spray exhibits a non-parallel angle relative to the airflow path defined by the at least partially enclosed space.

In various implementations and alternatives, the non-parallel angle is generally perpendicular to the airflow path defined by the at least partially enclosed space.

In various implementations and alternatives, the nozzle comprises a hollow fan nozzle.

In various implementations and alternatives, the nozzle is positioned to emit the agricultural spray in a direction that is substantially parallel to gravity.

In various implementations and alternatives, the at least one stimulus source comprises a pulsed stimulus source.

In various implementations and alternatives, the at least one stimulus source comprises a pulsed laser disposed outside of the at least partially enclosed space and the test section further comprises at least one of an aspheric lens, a positive or negative spherical lens, or combination of positive and negative concaved cylindrical lenses disposed outside of the at least partially enclosed space between the pulsed laser and the at least one surface.

In various implementations and alternatives, the at least one stimulus source comprises a continuous light source.

In various implementations and alternatives, the at least one stimulus source comprises a collimated light source.

In various implementations and alternatives, the at least one detector is positioned such that an imaging plane detected by the at least one detector is generally perpendicular to the portion of the agricultural spray.

In various implementations and alternatives, the at least one detector is positioned such that an imaging plane detected by the at least one detector is generally parallel to the portion of the agricultural spray.

In various implementations and alternatives, the test section comprises one or more lenses configured to collimate the stimulus emitted from the at least one stimulus source.

In various implementations and alternatives, the test section comprises a collection or condenser lens and an aperture. The collection or condenser lens and the aperture are positioned and configured to improve a resolution of the image detected by the at least one detector.

In various implementations and alternatives, the test section comprises one or more lenses positioned and configured to magnify the image detected by the at least one detector.

Features from the disclosed embodiments may be combined with one another, without limitation. In addition, other features and advantages of the present disclosure will become apparent to those of ordinary skill in the art through consideration of this detailed description and the drawings.

BRIEF DESCRIPTION OF THE DRAWINGS

The drawings illustrate several embodiments of the present disclosure, wherein identical reference numerals refer to identical or similar elements or features in different views or embodiments in the drawings.

DETAILED DESCRIPTION

The embodiments disclosed herein relate to test sections, wind tunnels including the test sections, and methods of using the test sections and the wind tunnels disclosed herein. In an embodiment, an example test section includes at least one surface defining an at least partially enclosed space. The at least partially enclosed space defines an airflow path for air to flow through. The test section also includes a nozzle disposed in the at least partially enclosed space. The nozzle is configured to spray an agricultural spray. The nozzle is positioned and configured to emit the agricultural spray so at least a portion of the agricultural spray exhibits a non-parallel angle relative to the airflow path defined by the at least partially enclosed space. The non-parallel angle of the agricultural spray may enable the detection of the bag rupture approach to droplet formation, a newly discovered mechanism of droplet formation disclosed herein. The test section also includes a stimulus source (e.g., light source) positioned to illuminate at least a portion of the agricultural spray adjacent to the nozzle. The test section further includes at least one detector positioned to image the portion of the agricultural spray that is adjacent to the nozzle. The stimulus source may illuminate and the detector may detect portions of the agricultural spray that are adjacent to the nozzle since the bag rupture approach to droplet formation occurs in the portion of the agricultural spray that are adjacent to the nozzle.

The test section and the wind tunnels disclosed herein may detect one or more spray characteristics of the agricultural spray before the agricultural spray is used in field tests and subsequently in field application. In an embodiment, the test section and the wind tunnels disclosed herein may detect and/or quantify one or more disadvantageous spray attributes of the agricultural spray. For example, agricultural sprays often produce driftable small droplets exhibiting a diameter of about 150 µm or less ("small droplets"). These small droplets are susceptible to off-target drift which may cause the agricultural spray to be deposited on unintended plant surfaces causing injury or harm to the vegetation. Traditional measures of reducing the quantity of small droplets formed from the agricultural spray, such as by nozzle design or chemical adjuvant additive, often increases the number of ultra-coarse droplets exhibiting a diameter greater than 622 µm ("ultra-coarse droplets"). High rates of ultra-coarse droplets diminish the area coverage of the agricultural spray. The reduced area coverage has been linked to reduced efficacy of the agricultural spray performance and the evolution of chemical-resistance in commonly-treated weed species.

The number of small droplets and/or ultra-coarse droplets may depend on the atomization mechanism that forms the droplets. It was believed that spray sheets formed from flat fan nozzles, the most common nozzle class in agricultural applications, and other types of nozzles were dominated by two atomization mechanisms: the wave instability and perforation approaches of droplet formation. For the wave instability approach, ligament formation may be produced by aerodynamically-induced wave instabilities. These instabilities grow to generate wave fronts within the spray sheet region just downstream of the nozzle. These wave fronts form continuous thick and thin bands. The thin bands eventually collapse, forming ligaments from the thick bands, which collapse into droplets. In the perforation approach, the spray sheet may perforate, generating voids within the spray sheet which grow to form a web-like structure of ligaments. This ligament structure eventually continues to collapse into droplets. Regardless of the atomization mechanism for these spray sheets, a wide geometric spectrum of droplet sizes is produced.

The number of small droplets and/or ultra-coarse droplets were tested in wind tunnels including test sections that differ from the test sections disclosed herein. For example, the previously used test sections included a flat fan nozzle configured to emit the agricultural spray in a spray sheet that extends parallel to air flowing in the previously used test section. The previously used test section also included a light source and a detector that are positioned to illuminate and image a portion of the spray sheet sufficiently spaced from the nozzle that the wave instability and perforation approaches of droplet formation have formed the droplets. This allowed the light source and the detector to detect and quantify the number of small and ultra-coarse droplets formed from the agricultural spray.

However, using agricultural sprays that included polymers (e.g., agricultural sprays including drift reduction adjuvant compositions that, in theory, are configured to minimize the formation of small droplets) in field tests demonstrated that the agricultural sprays, under certain circumstances, formed more small droplets than the same agricultural spray used in the previously used test section. To determine the cause of the greater than expected number of small droplets during field tests, it was recently discovered that a third atomization mechanism may cause the formation of small droplets: the bag rupture approach to droplet formation. The bag rupture approach to droplet formation is caused by a polymer in the spray tank composition. The bag rupture approach is caused by the formation of a continuous liquid phase in the spray sheet near the nozzle. A portion of the continuous liquid phase of the spray sheet is subjected to hydrodynamic forces associated with the fluid discharge and certain surrounding environmental forces (e.g., aerodynamic forces of the environment) which may cause a formation of a thin membraned semi-spherical protrusion, which is referred to as a “bag” herein. Upon rupture, the thinnest portion of the bag membrane atomizes thereby generating a large number of small droplets ejected in a direction generally perpendicular to the spray sheet. These small droplets are susceptible to drift because the small droplets trajectories are aligned with the environmental wind conditions (i.e., not oriented toward the target location) and the small droplets are dominated by environmental forces (e.g., aerodynamic forces) and not by gravitational forces. The remainder of the bag membrane further collapses into various ligament geometries and contrails. In an example, circumstances that may cause the bag rupture approach includes air movement around the continuous liquid phase of the spray sheet induced by atmospheric wind conditions and/or travel speed of an applicator of the agricultural spray (i.e., the speed that a tractor or other device that includes the nozzle moves relative to a ground surface), or a spray sheet discharging in a direction perpendicular to the surrounding air flow.

The test section and the wind tunnels disclosed herein can detect the bag rupture approach to droplet formation for at least several reasons. For example, the nozzle emits the agricultural spray in a spray sheet so at least a portion of the spray sheet exhibits a non-parallel angle relative to the airflow path of the enclosed space and, thus, the spray sheet is oriented at a non-parallel angle relative to the air flowing through the test section. The non-parallel angle allows the test section to replicate cross-wind conditions that the agricultural sprays are commonly subjected to during field tests that cause the bag rupture approach to droplet formation. Further, the stimulus source illuminates and the detector images portions of the spray sheet that are proximate to the nozzle. This allows the detector to detect the bag rupture approach to droplet formation since the spray sheet only forms the bag near the nozzle.

FIGS. 1A and 1B are cross-section and top plan views, respectively, of a test section 100, according to an embodiment. The test section 100 includes at least one surface defining an enclosed space 102. The test section 100 includes at least one nozzle 104 disposed in the enclosed space 102 configured to dispense an agricultural spray 106 therefrom. The test section 100 also includes at least one stimulus source 108 configured to emit a stimulus 110 that illuminate at least a portion 114 (shown in phantom lines) of the agricultural spray 106 that is proximate to the nozzle 104. The test section 100 also includes a detector 112 configured to image at least the portion 114 of the agricultural spray 106 that is proximate to the nozzle 104. In the illustrated embodiment, the stimulus source 108 and the detector 112 are positioned outside of the enclosed space 102. The at least one surface includes at least one transparent section 116 which allows the stimulus 110 to enter the enclosed space 102 and the detector 112 to image the portion 114 of the agricultural spray 106. However, it is noted that, in some embodiments, at least one of the stimulus source 108 or the detector 112 may be disposed in the at least one surface and/or disposed in the enclosed space 102.

In an embodiment, the at least one surface (e.g., at least one wall) that defines that enclosed space 102 may include a plurality of surfaces. In an example, as illustrated, the at least one surface may include a top surface 118, an opposing bottom surface 120, and two lateral surfaces 122 extending between the top surface 118 and the bottom surface 120. Each of the top surface 118, the bottom surface 120, and the two lateral surfaces 122 may be substantially planar. Forming the top surface 118, the bottom surface 120, and the two lateral surfaces 122 to be substantially planar may facilitate construction of the test section 100 since such components are readily available and, optionally, may be connected together using commonly available mechanical attachment devices (e.g., L-shapes brackets). Further, as discussed in more detail below, forming the top surface 118, the bottom surface 120, and the two lateral surfaces 122 to be substantially planar may allow the enclosed space 102 to exhibit a substantially continuous cross-sectional shape which may improve the uniformity of air 126 (shown schematically with an arrow FIG. 1B) flowing through the enclosed space 102. However, it is noted that at least one of the top surface 118, the bottom surface 120, or the two lateral surfaces 122 may not be substantially planar. For example, at least one of the top surface 118, the bottom surface 120, or the two lateral surfaces 122 may be curved (e.g., convexly or concavely curved) and/or, as will be discussed in more detail below, may include one or more recesses formed therein. Further, it is understood that the plurality of surfaces may include less than or more than four surfaces, depending on the application, and that these surfaces may exhibit the same characteristics discussed regarding the top surface 118, the bottom surface 120, and the two lateral surfaces 122. For example, the at least one surface that defines the enclosed space may include a single surface (e.g. continuous) formed from a pipe.

The cross-sectional shape of the enclosed space 102 may depend on the number of surfaces that define the enclosed space 102. For example, as illustrated, the enclosed space 102 exhibits a generally square or rectangular shape because the enclosed spaced 102 is defined by four surfaces (e.g., the top surface 118, the bottom surface 120, and the two lateral surfaces 122). Forming the enclosed space 102 to exhibit the generally square or rectangular shape facilitates operation of the test section 100. For example, unlike some other shapes, the generally square or rectangular shape of the enclosed space 102 causes the bottom surface 120 and the two lateral surfaces 122 to be sufficiently spaced from the nozzle 104 these surfaces are unlikely to interact with the agricultural spray 106 until all the droplets have been formed. Further, the generally square or rectangular shape of the enclosed space 102 allows the two lateral surfaces 122 to be generally parallel to a direction that the nozzle 104 emits the agricultural spray 106 (e.g., at least one of generally parallel to gravity or perpendicular to a ground surface) which may allow the stimulus 110 entering and/or leaving the enclosed space 102 through the transparent sections 116 to be perpendicular to the transparent sections 116. The perpendicular angle between the stimulus 110 and the transparent sections 116 may reduce any effect caused by refracting the stimulus 110. However, it is noted that enclosed space 102 may exhibit a generally non-square or non-rectangular shape, depending on the application, without limitation. Further, it is noted that the stimulus 110 entering and/or exiting the enclosed space 102 may exhibit a non-perpendicular angle relative to the transparent sections 116.

In an embodiment, the enclosed space 102 may exhibit a cross-sectional shape and cross-section dimension(s) that do not vary along a length of the enclosed space 102. Not varying the cross-sectional shape and the cross-section dimension(s) of the enclosed space 102 may increase the uniformity of the air 126 flowing through the enclosed space 102 (e.g., reduce turbulent air flow). The increased uniformity of the air 126 flowing through the enclosed space 102 may improve the repeatability of any test performed in the test section 100. However, in some embodiments, the enclosed space 102 may exhibit a cross-section shape and/or cross-section dimension(s) that vary along at least a portion of the length of the enclosed space 102. In an example, as will be discussed below, the cross-sectional shape of the enclosed space 102 may vary to include recesses (e.g., recess 124). In an example, the cross-sectional dimension(s) of the enclosed space 102 may vary to modify the speed of the air 126 flowing through the test section 100. For instance, decreasing a cross-sectional dimension may increase the speed of the air 126 while increasing a cross-sectional dimension may decrease the speed of the air 126.

In an embodiment, as illustrated, the enclosed space 102 may be completely enclosed. Completely enclosing the enclosed space 102 may increase the uniformity of the air 126 flowing through the enclosed space 102. However, the enclosed space 102 may only be partially enclosed. In an example, the at least one surface that defines the enclosed space 102 may include one or more unoccupied openings that may allow devices to be inserted into the enclosed space 102 during operation or otherwise provide access to the enclosed space 102 during operation.

As previously discussed, at least one of the surface that define the enclosed space 102 may define at least one recess therein. In an embodiment, as illustrated, the bottom surface 120 defines a recess 124 therein. The recess 124 may be configured to receive at least a portion of the agricultural spray 106 dispensed into the enclosed space 102 and may channel the agricultural spray 106 towards an outlet (not shown) thereby removing the agricultural spray 106 from the enclosed space 102. The bottom surface 120 may include a slightly tapered topography to channel the agricultural spray 106 towards the recess 124. In an embodiment, the at least one surface may define one or more recesses to accommodate a spray angle of the agricultural spray. For example, the two lateral surfaces 122 may define one or more recesses near an intersection of the two lateral surfaces 122 and the bottom surface 120 to decrease the likelihood that the two lateral surfaces 122 contact the agricultural spray 106.

As previously discussed, the at least one surface that defines the enclosed space 102 may include at least one transparent section 116. The transparent section 116 allows at least one individual or device located outside of the enclosed space 102 to view the enclosed space 102 during operation. In an embodiment, as illustrated, both the stimulus source 108 and the detector 112 are disposed outside of the enclosed space 102. In such an embodiment, the at least one transparent section 116 may include a first transparent section formed in one of the two lateral surfaces 122 and a second transparent section formed in the other of the two lateral surfaces 122. The stimulus source 108 may be positioned relative to the first transparent section so the stimulus 110 enters the enclosed space 102 through the first transparent section. The stimulus 110 that enters the enclosed space 102 may illuminate at least the portion 114 of the agricultural spray 106 that is adjacent to the nozzle 104. The detector 112 may be positioned relative to the second transparent section so the detector 112 images at least the portion 114 of the agricultural spray 106 that is adjacent to the nozzle 104 through the second transparent section. The illustrated configuration is beneficial since the stimulus 110 passes through the agricultural spray 106 which may increase the resolution of the image detected by the detector 112. However, it is noted that the transparent section 116 and the position of the stimulus source 108 and the detector 112 may differ from the illustrated embodiment. For example, the transparent section 116 may only include a single transparent section (e.g., the stimulus source 108 is positioned to emit the stimulus 110 through the single transparent section and the detector 112 images the enclosed space 102 through the single transparent section), the transparent section 116 includes three or more transparent sections, or at least one of the stimulus source 108 or the detector 112 are disposed in the enclosed space 102.

As previously discussed, the enclosed space 102 defines an airflow path for air 126 (schematically illustrated with an arrow in FIG. 1B) to flow during operation. Generally, during operation, the average direction that the air 126 flows through the enclosed space 102 is parallel to the airflow path of the enclosed space 102. As such, as used herein, the average direction that the air 126 flows through the enclosed space 102 and the airflow path of the enclosed space 102 may be used interchangeably without limitation. However, it is noted that the average direction that the air 126 flows through the enclosed space 102 may vary slightly (e.g., less than 5° or less than 1°) from the airflow path due to turbulent air flow, recesses in the at least one surface, etc.

As previously discussed, the at least one nozzle 104 may be disposed in the enclosed space 102 and is configured to dispense the agricultural spray 106 into the enclosed space 102. In an embodiment, the nozzle 104 is positioned and configured to dispense the agricultural spray 106 in a direction at least one of parallel to gravity or perpendicular to ground (e.g., perpendicular to at least a portion of the bottom surface 120). Dispensing the agricultural spray 106 in a direction that is parallel to gravity or perpendicular to the ground mimics conventional methods of dispensing agricultural sprays on crops and is conducive to detecting the formation of bags in the spray sheet of the agricultural spray 106. However, the nozzle 104 may be positioned and configured to dispense the agricultural spray 106 in a direction not at least one of parallel to gravity or perpendicular to the ground.

In an embodiment, the nozzle 104 is a flat fan nozzle since flat fan nozzles are commonly used to dispense agricultural sprays and the spray fan formed from the flat fan nozzle is conducive to forming droplets via the bag rupture approach. In an embodiment, the nozzle 104 may include a hollow cone nozzle since the spray fan formed from the hollow cone nozzle is conducive to forming droplets via the bag rupture approach. In an embodiment, the nozzle 104 may include nozzles manufactured by TeeJet (TTI 11004 nozzle, XR11002—XR TeeJet Extended Range Flat Spray Tip, AIXR11004—AIXR TeeJet Spray Tip), Hypro, Greenleaf, Wilger, Lechler, including nozzle models such as AIXR, AI, TT, UCD and so on. It is noted that, while these nozzles are configured to dispense agricultural sprays, it is noted that these nozzles may also dispense other fluids (e.g., the test section 100 may test non-agricultural spray liquids).

In an embodiment, the flow rates of the agricultural spray 106 through the nozzle 104 may be about 0.0125 gallon per minute ("gpm") to about 3.0 gpm, such as about 0.2 gpm to about 1.5 gpm, or about 0.0126 gpm to about 2.0 gpm. In an embodiment, the nozzle 104 may emit the agricultural spray 106 at a spray angle of about 65° to about 140°, up to about 140°, about 90°, about 100°, about 110°, about 120°, about 130° or about 140°. In an embodiment, the nozzle 104 may be operated at up to 200 psi fluid pressure, or up to about 150 psi, up to about 115 psi, about 15 psi to about 115 psi, about 30 psi to about 60 psi fluid pressure, or about 15 psi, about 20 psi, about 30 psi, about 40 psi, about 50 psi, about 60 psi, about 70 psi, about 80 psi, about 90 psi, about 100 psi, about 110 psi fluid pressure, or any integer range of the aforementioned pressure levels (e.g., about 15 psi to about 60 psi).

Figure 1A:
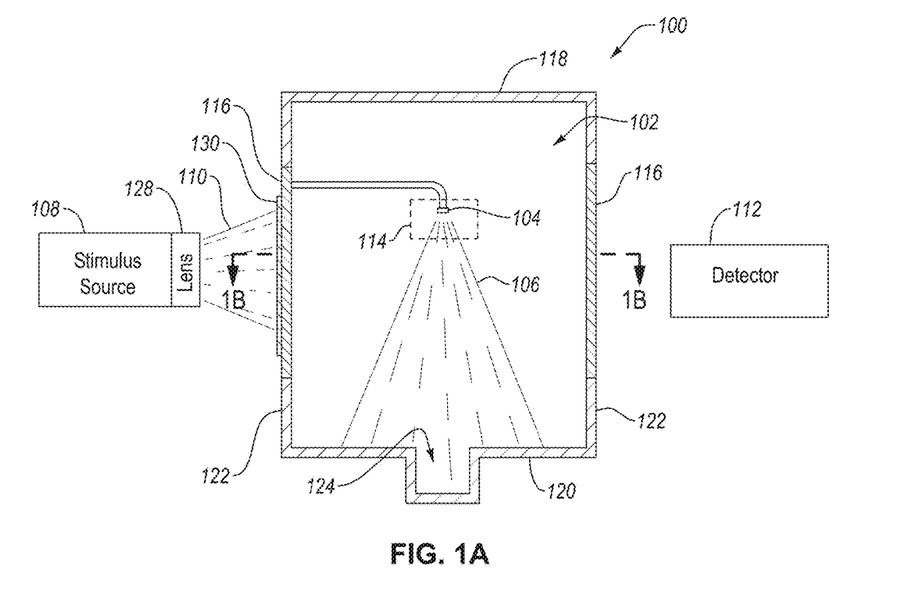
FIGS. 1A and 1B are cross-section and top plan views, respectively, of a test section 100, according to an embodiment.
Figure 1B:
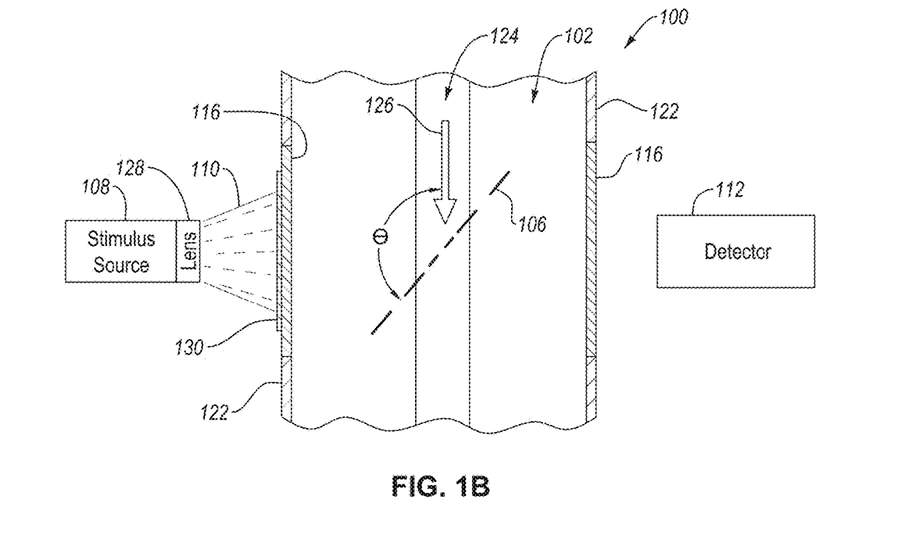

Referring to FIG. 1B, the nozzle 104 is positioned and configured to dispense the agricultural spray 106 so at least a portion of a spray sheet of the agricultural spray 106 exhibits an spray orientation angle θ relative to the direction that the air 126 flows through the enclosed space 102. In a top plan view, the spray orientation angle θ is the angle measured clockwise from the spray sheet of the agricultural spray 106 to the average direction that the air 126 intersects the spray sheet. Additionally, the nozzle 104 is positioned and configured to dispense the agricultural spray 106 so at least a portion of a spray sheet of the agricultural spray 106 exhibits the spray orientation angle θ relative to the airflow path of the enclosed space 102 since, as previously discussed, the direction that the air 126 flows through the enclosed space 102 and the airflow path of the enclosed space 102 are substantially the same. In an example, when the nozzle 104 is a flat fan nozzle, all of the spray sheet of the agricultural spray exhibits the spray orientation angle θ relative to the direction that the air 126 flows through the enclosed space 102. In an example, when the nozzle 104 is a hollow cone nozzle or another nozzle that forms a curved spray sheet, only a portion of the spray sheet of the agricultural spray 106 may exhibit the spray orientation angle θ.

Unlike conventional wind tunnels, the nozzle 104 is positioned and configured so the spray orientation angle θ is non-parallel to the direction that the air 126 flows through the enclosed space 102. Selecting the spray orientation angle θ to be non-parallel to the direction that the air 126 flows through the enclosed space 102 allows the spray sheet of the agricultural spray 106 to be exposed to simulated crosswinds. It is the simulated crosswinds that may cause the spray sheet of the agricultural spray 106 to exhibit the bag rupture approach to droplet formation. For example, the spray orientation angle θ may be selected to be about 1° to about 179°. However, the spray orientation angle θ is more preferably selected to be about 10° to about 170° and, even more preferably, about 20° to about 160° or about 30° to about 150° since the spray sheet of the agricultural spray 106 is more likely to exhibit the bag rupture approach to droplet formation the closer the spray orientation angle θ is to 90°. In an example, the spray orientation angle θ may be selected to be about 10° to about 30°, about 20° to about 40°, about 30° to about 50°, about 40° to about 60°, about 50° to about 70°, about 60° to about 80°, about 70° to about 90°, about 80° to about 100°, about 90° to about 110°, about 100° to about 120°, about 110° to about 130°, about 120° to about 140°, about 130° to about 150°, about 140° to about 160°, or about 150° to about 170°.

In an embodiment, the spray orientation angle θ may be selected so the spray sheet of the agricultural spray 106 exhibits a selected orientation relative to the detector 112. In an example, the spray sheet of the agricultural spray 106 may be oriented so the image plane detected by the detector 112 is generally parallel to the spray sheet which may allow the detector 112 to detect the formation and rupture of bags along a width of the spray sheet. In such an example, the spray orientation angle θ may be selected to be generally perpendicular (e.g., about 70° to about 110° or about 80° to about 100°) to the direction that the air 126 flows through the enclosed space 102 when the detector 112 is oriented at a generally perpendicular angle relative to the direction that the air 126 flows through the enclosed space 102. In an example, the spray sheet of the agricultural spray 106 may be oriented so the image plane detected by the detector 112 is generally perpendicular to the spray sheet which may allow the detector 112 to detect the edge of the spray sheet and, more particularly, the profile of the bags formed in the spray sheet. In such an example, the spray orientation angle θ may be selected to be nearly parallel (e.g., about 5° to about 35° or about 10° to about 30°) to the direction that the air 126 flows through the enclosed space 102 when the detector 112 is oriented at a generally perpendicular angle relative to the direction that the air 126 flows through the enclosed space 102. In an embodiment, the detector 112 is moved (e.g., moved manually or with an actuator) instead of or in conjunction with selecting the spray orientation angle θ to obtain a desired image.

In an embodiment, the nozzle 104 may be configured to be selectively repositioned (e.g., rotated) to controllably change the spray orientation angle θ. For example, FIG. 1B illustrates that the spray orientation angle θ is a generally obtuse angle. However, FIG. 1C, which is a top plan view of the test section 100 after the nozzle 104 is selectively repositioned, the spray orientation angle θ is about 90°. The nozzle 104 may be configured to be selectively repositioned using any suitable method. In an example, the nozzle 104 may be configured to be manually repositioned by an individual disposed in the enclosed space 102. In such an example, the nozzle 104 may only be repositioned when the test section 100 is being used. In an example, the nozzle 104 may be coupled to an actuator, such as an electric motor, which is configured to controllably reposition the nozzle 104. In such an example, the nozzle 104 may be repositioned during operation of the test section 100 (e.g., while the nozzle 104 is dispensing the agricultural spray 106) thereby allowing the test section 100 to test the agricultural spray 106 at multiple spray orientation angles θ in a single test. It is noted that, in some embodiments, the nozzle 104 may be moved up and/or down (e.g., either manually or using an actuator).

In an embodiment, the test section 100 and/or a wind tunnel that includes the test section 100 may include a fluid reservoir (not shown), such as a tank, that is configured to hold the agricultural spray 106. In such an embodiment, the nozzle 104 may be fluidly coupled to the fluid reservoir so the nozzle 104 may receive and dispense the agricultural spray 106. Examples of the agricultural sprays that may be stored in the fluid reservoir are disclosed in U.S. patent application Ser. No. 15/857,145 filed on Dec. 28, 2017, U.S. patent application Ser. No. 16/023,790 filed on Jun. 29, 2018, and U.S. Patent Application entitled "Methods of Using Drift Reduction Adjuvant Compositions" Ser. No. 16/198,384, the disclosure of each of which is incorporated herein, in its entirety, by this reference. It is noted that, in an embodiment, the fluid reservoir may include liquid that is not an agricultural spray. In such an embodiment, the nozzle 104 may receive and dispense the liquid and the test section 100 may test liquids that are not agricultural sprays.

The stimulus source 108 may include any suitable device that may illuminate the portion 114 of the agricultural spray 106 in a manner that allows the detector 112 to detect the portion 114 of the agricultural spray 106. Generally, the stimulus source 108 is an electromagnetic source configured to emit visible light. Examples of the stimulus source 108 that emit visible light includes a light emitting diode ("LED"), a flash bulb, a halogen light, a mercury light, a xenon lamp, or a laser. However, it is noted that the stimulus source 108 may include an electromagnetic source configured to emit non-visible light (e.g., ultraviolet light or infrared light) or another stimulus source (e.g., acoustic source). In an embodiment, the stimulus source 108 may include a single stimulus source (as shown) or a plurality of stimulus sources.

In an embodiment, as illustrated, the stimulus source 108 is disposed outside of the enclosed space 102. Disposing the stimulus source 108 outside of the enclosed space 102 may prevent the agricultural spray 106 from inadvertently coming in contact with the stimulus source 108. For example, contacting the stimulus source 108 with the agricultural spray 106 may dirty the stimulus source 108 thereby reducing the intensity of the stimulus 110 emitted from the stimulus source 108 and/or prevent the agricultural spray 106 from damaging the electronics of the stimulus source 108. However, as previously discussed, the stimulus source 108 may be at least partially disposed in the enclosed space 102.

In an embodiment, the stimulus source 108 is a pulsed light source, such as a pulsed laser, a pulsed LED, or a flash bulb. The pulsed light source may discharge a large amount of light (i.e., high intensity) during a short period of time. The large amount of light allows for a high resolution image, especially when the background light levels are low. In an embodiment, the stimulus source 108 is a continuous light source, such as an LED light source, a halogen light source, a mercury light source, or a xenon lamp. The continuous light source may be used, for example, when the desired imaging frame rate is too fast for a pulsed light source to recharge.

In an embodiment, the stimulus source 108 includes a laser, such as a pulsed laser. In such an embodiment, the stimulus source 108 may include at least one of an aspheric lens 128, a positive or negative (concave, convex) spherical lens, a combination of positive and negative concave lenses, or other optical elements which causes the laser beam to diverge. Diverging the laser beam allows the stimulus 110 emitted from the stimulus source 108 to illuminate the portion 114 of the agricultural spray 106 instead of just a small dot.

In an embodiment, the stimulus source 108 may be configured to move. For example, the stimulus source 108 may include or be operably coupled to an actuator that may move the stimulus source 108. For instance, the actuator may change the position of the stimulus source 108 relative to the enclosed space 102 or change the direction that the stimulus source 108 emits the stimulus 110.

In an embodiment, the test section 100 may include a diffuser 130 disposed between the stimulus source 108 and the agricultural spray 106. For example, the diffuser 130 may be positioned on the transparent section 116 that is positioned between the agricultural spray 106 and the stimulus source 108. The diffuser 130 may soften the stimulus 110 emitted from the stimulus source 108 thereby reducing the harsh light and hard shadows detected by the detector 112 which may increase the resolution of image detected by the detector 112. The diffuser 130 may also cause a single stimulus source to behave like a plurality of stimulus sources that illuminate the agricultural spray 106 from many angles thereby increasing the contrast of the detected image. Further, in some embodiments, the diffuser 130 may provide a uniform background for the image detected by the detector 112 which may increase the contrast of the detected image.

The type of detector 112 that is selected to image the portion 114 of the agricultural spray 106 may depend on the stimulus 110 emitted from the stimulus source 108. For example, the detector 112 may include a camera or other detector of visible light if the stimulus 110 is visible light or may include an ultraviolet or infrared detector if the stimulus 110 is ultraviolet light or infrared light, respectively.

In an embodiment, the detector 112 may include a high frame rate camera or a low frame rate camera. The low frame rate camera may allow the capture high resolution (>20 megapixel) images which allows for the close examination of images (e.g. to identify the presence of bags). The high speed camera may offer the temporal resolution to examine the formation and collapse of a bag membrane but may lack the resolution (<4 megapixels) for close study.

In an embodiment, as illustrated, the detector 112 is disposed outside of the enclosed space 102. Disposing the detector 112 outside of the enclosed space 102 may prevent the agricultural spray 106 from inadvertently coming in contact with the detector 112. For example, contacting the detector 112 with the agricultural spray 106 may dirty a lens of detector 112 thereby reducing the resolution of the image detected by the detector 112 and/or damage the electronics of the detector 112. However, as previously discussed, the detector 112 may be at least partially disposed in the enclosed space 102.

In an embodiment, the detector 112 may be configured to move. For example, the detector 112 may include or be operably coupled to an actuator that may move the detector 112. For instance, the actuator may change the position of the detector 112 relative to the enclosed space 102 or change the direction that the detector 112 faces.

Figure 2:
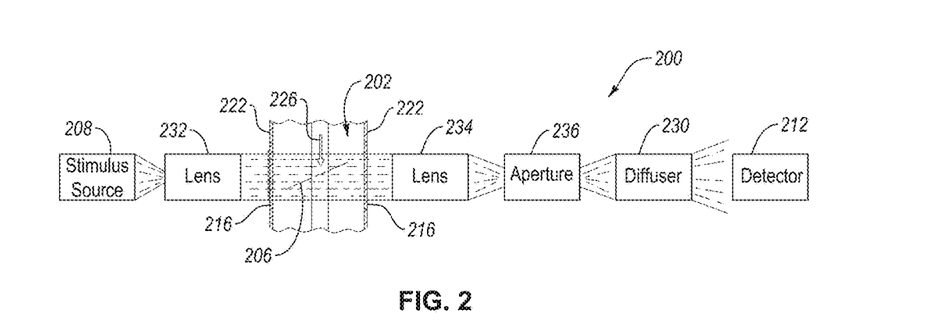
FIG. 2 is a schematic top plan view of a test section 200, according to an embodiment.

In an embodiment, as illustrated, the test section 100 may only include a single detector. In another embodiment, the test section 100 may include a plurality of detectors. The plurality of detectors may have different positions so the plurality of detectors image different portions of the agricultural spray 106 simultaneously. For example, one of the plurality of detectors may be positioned so the detected image plane is generally parallel to the spray sheet of the agricultural spray 106 while another one of the plurality of detectors may be positioned so the detected image plane is generally perpendicular to the spray sheet of the agricultural spray 106. Further, the plurality of detectors may enable the test section 100 to both detect the bag rupture approach to droplet formation and quantify the size of the droplets formed from the agricultural spray 106. For instance, at least one of the plurality of detectors may be positioned to image the portion 114 of the agricultural spray 106 thereby detecting the bag rupture approach to droplet formation while at least one other detector may be positioned to image a portion of the agricultural spray 106 sufficiently spaced from the nozzle 104 to quantifiably detect the size of the droplets formed from the agricultural spray 106.

As previously discussed, the stimulus source 108 is positioned and configured to illuminate at least the portion 114 of the agricultural spray 106 and the detector 112 is positioned and configured to detect at least the portion 114 of the agricultural spray 106. In an example, the portion 114 of the agricultural spray 106 includes a region of the agricultural spray 106 initially exiting the nozzle 104 that forms the continuous sheet-like portion to define an initial spray pattern, such as a fan-shaped pattern or a cone-shaped pattern. In such an example, the portion 114 of the agricultural spray 106 may also include additional portions of the agricultural spray 106 extending from the initial spray pattern, such as ligament structures formed from the initial spray pattern. In an example, the portion 114 of the agricultural spray 106 extends from the nozzle 104 and includes the area of primary atomization and, optionally, an area of secondary atomization. In such an example, the portion 114 allows the atomization of the continuous liquid phase of the agricultural spray 106 to be detected (e.g., visually studied). In an example, the portion 114 of the agricultural spray 106 extends from the nozzle 104 until at least the continuous liquid phase of the agricultural spray 106 collapses into ligament structures. In such an example, the portion 114 may also include regions of the agricultural spray 106 after the collapse of the ligament structures. In an example, the portion 114 of the agricultural spray 106 includes all of the agricultural spray 106 except for regions of the agricultural spray 106 after substantially full and complete atomization (i.e., substantially no additional droplet formation occurs) is achieved. In an example, the portion 114 of the agricultural spray 106 extends from the nozzle 104 to about 1 to about 3 times the breakup length of the agricultural spray 106. In an example, a horizontal dimension of the portion 114 of the agricultural spray 106 is sufficient to adequately capture the entirety of the agricultural spray 106 for a given downstream length. In such an example, the horizontal dimension of the portion 114 of the agricultural spray 106 is a function of the spray angle of the nozzle 104. In an example, a horizontal dimension of the portion 114 of the agricultural spray 106 does not capture the entirety of the agricultural spray 106 for a given downstream length. In such an example, the horizontal dimension of the portion 114 may include at least 10%, at least 25%, at least 50%, at least 75%, or at least 90% of the entirety of the agricultural spray 106 for a given downstream length.

FIG. 2 is a schematic top plan view of a test section 200, according to an embodiment. Except as otherwise disclosed, the test section 200 is the same as or substantially similar to any of the test sections disclosed herein. For example, the test section 200 includes at least one surface 222 defining an enclosed space 202. The test section 200 further includes at least one nozzle (not shown) configured to dispense an agricultural spray 206 at a desired angle relative to the flow of air 226 through the enclosed space 202. Additionally, the test section 200 includes a stimulus source 208 and a detector 212.

The test section 200 includes one or more optical elements configured to facilitate operation of the test section 200. The one or more optical elements may include one or more lenses, one or more apertures, one or more diffusers, or any other suitable optical element.

In an embodiment, the one or more optical elements may include a first lens 232 configured to collimate the stimulus 210 emitted from the stimulus source 208 since the collimating the stimulus 210 may improve the resolution of the image detected by the detector 212. Typically, the first lens 232 may be spaced from the stimulus source 208 though the first lens 232 may be adjacent to or integrally formed with the stimulus source 208. The first lens 232 is positioned between the stimulus source 208 and the agricultural spray 206 so the stimulus 210 that illuminates the agricultural spray 206 is collimated. Generally, the first lens 232 is disposed outside of the enclosed space 202 thereby preventing the agricultural spray 206 from coating and dirtying the first lens 232. However, it is noted that the first lens 232 may form the transparent section 216 of the at least one surface 222 that defines the enclosed space 202 or may be disposed in the enclosed space 202.

In an embodiment, the one or more optical elements may include a second lens 234 that is a collection lens or a condenser lens that causes the collimated light to converge. In such an embodiment, the one or more optical element may also include an aperture 236 (e.g., iris) positioned in series with and closer to the detector 212 than the second lens 234. The aperture 236 may limit the amount of the stimulus 210 that reaches the detector 212. Both the second lens 234 and the aperture 236 may be positioned between the agricultural spray 206 and the detector 212. The second lens 234 and the aperture 236, collectively, may improve the resolution of the image detected by the detector 212. Generally, both the second lens 234 and the aperture 236 are disposed outside of the enclosed space 202 thereby preventing the agricultural spray 206 from coating and dirtying the second lens 234 and the aperture 236. However, it is noted that the second lens 234 may form the transparent section 216 of the at least one surface 222 or at least one of the second lens 234 and the aperture 236 may be disposed in the enclosed space 202. Further, typically, the second lens 234 and the aperture 236 are spaced from the detector 212 though at least one of the second lens 234 or the aperture 236 may be adjacent to or integrally formed with the detector 212.

In an embodiment, the one or more optical elements may include a diffuser 230. The diffuser 230 may be disposed on the transparent section 216 of the surface 222, as shown in FIGS. 1A-1C. However, as illustrated, the diffuser 230 may be disposed between the agricultural spray 206 and the detector 212 thereby softening the light detected by the detector 212 and improving the contrast of the image detected by the detector 212. In an example, the diffuser 230 may be a diffusion filter attached to the detector 212.

The test section 100 may include additional optical elements not illustrated in FIG. 2. For example, the test section 100 may include at least one lens configured to magnify the portions of the agricultural spray 206 detected by the detector 212, one or more aspheric lenses as previous disclosed herein, one or more positive and/or negative spherical lenses, one or more positive and/or negative concaved cylindrical lenses, one or more mirrors, one or more optical filters, one or more polarizers, or any other suitable optical element.

As previously discussed, in some embodiments, at least one of the first lens 232, the second lens 234, the aperture 236, the diffuser 230, or the one or more additional optical elements of the test section 200 may be spaced from the enclosed space 202. The position of the first lens 232, the second lens 234, the aperture 236, the diffuser 230, or the one or more additional optical elements, relative to the enclosed space 202, may depend on the position of the stimulus source 208 and the detector 212 relative to the enclosed space 202. For example, the stimulus source 208 may be positioned on a first lateral area that is spaced from the enclosed space 202 and the detector 212 may be positioned on second lateral area that is spaced from the enclosed space 202. The second lateral side may be on an opposing side of the enclosed space 202 than the first lateral area. In such an embodiment, the first lens 232 may be positioned on the first lateral area between the stimulus source 208 and the enclosed space 202 and the first lens 232 may be discrete from the stimulus source 208. As such, the stimulus 210 emitted from the stimulus source 208 passes through the first lens 232 before the stimulus 210 illuminates the agricultural spray 206. Further, the second lens 234 and the aperture 236 may be positioned in the second lateral area between the enclosed space 202 and the detector 212 which may improve a resolution of any image that is detected by the detector 212. The second lens 234 and the aperture 236 may be discrete from the detector 212. As previously discussed, the diffuser 230 may be positioned on either the first or second lateral area of the test section 200, depending on the embodiment, and also may be discrete from the stimulus source 208 and the detector 212.

Figure 3:
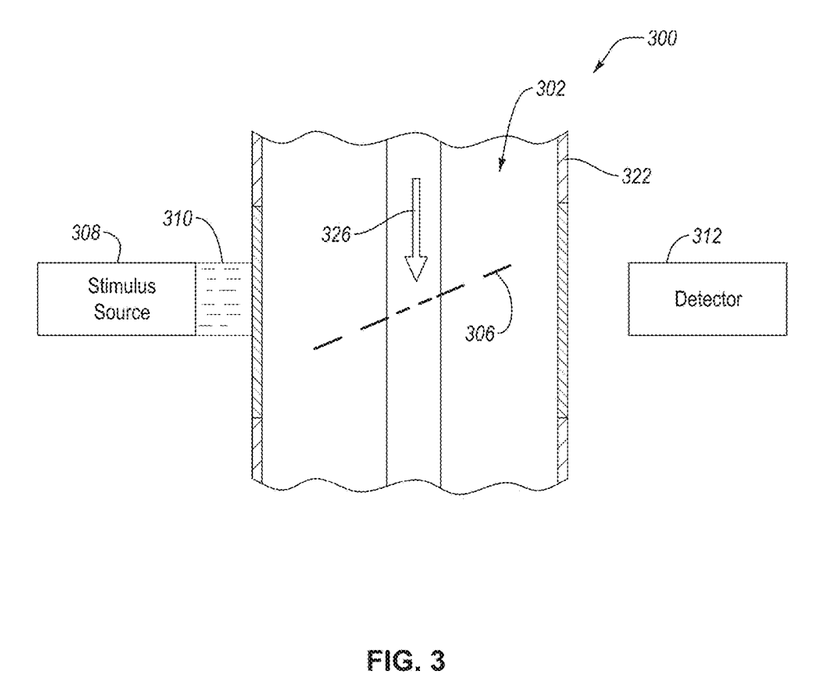
FIG. 3 is a schematic top plan view of a test section 300, according to an embodiment.

FIG. 3 is a schematic top plan view of a test section 300, according to an embodiment. Except as otherwise disclosed herein, the test section 300 is the same as or substantially similar to any of the test sections disclosed herein. For example, the test section 300 includes at least one surface 322 defining an enclosed space 302. The test section 300 further includes at least one nozzle (not shown) configured to dispense an agricultural spray 306 at a desired angle relative to the flow of air 326 through the enclosed space 302. Additionally, the test section 300 includes a stimulus source 308 and a detector 312.

The stimulus source 308 is configured to emit a collimated stimulus 310 which may simplify the test section 300 relative to the other test sections disclosed herein. For example, the collimated stimulus 310 may eliminate the need for a lens to collimate the stimulus 310 (e.g., first lens 232 of FIG. 2). Further, the collimated stimulus 310 may eliminate the need for a diffuser (e.g., diffuser 130 or 230 of FIGS. 1A-2) so long as nothing causes significant divergence or convergence of the collimated stimulus 310.

Figure 4:
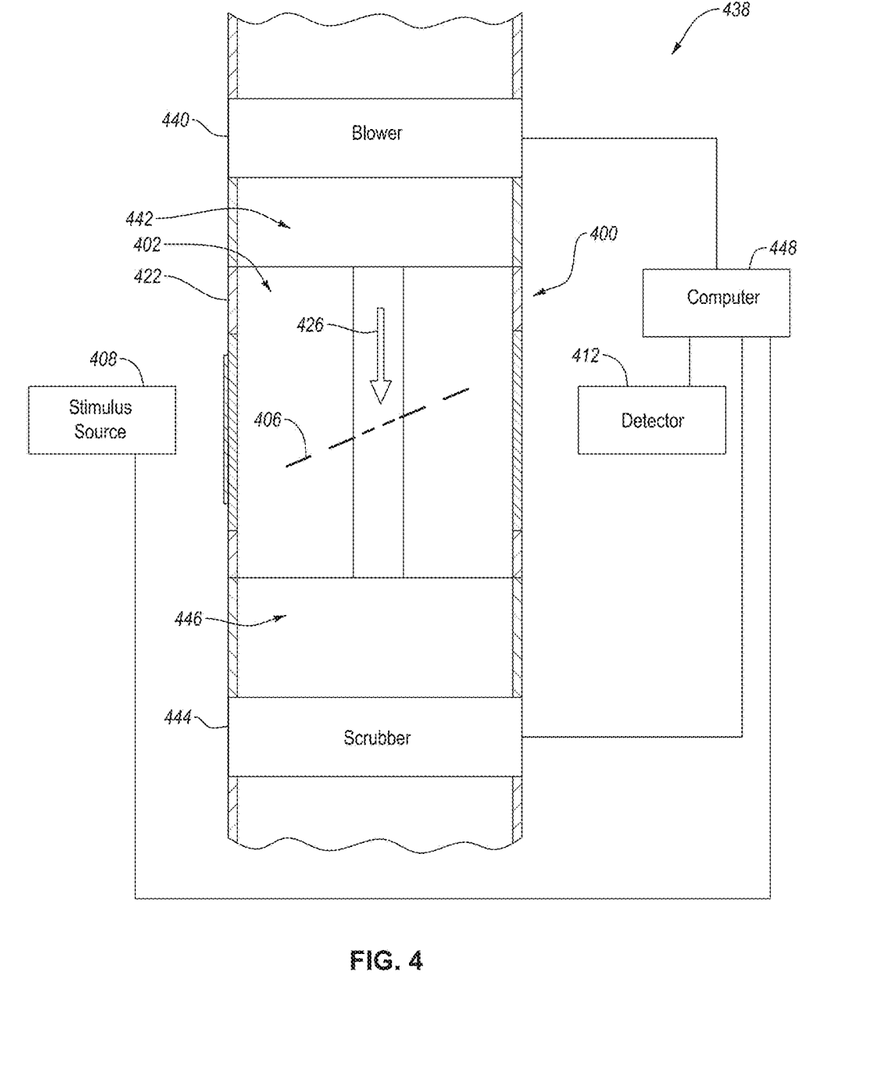
FIG. 4 is a schematic top plan view of an example wind tunnel 438, according to an embodiment.

The test sections disclosed herein may be used in any suitable wind tunnel. FIG. 4 is a schematic top plan view of an example wind tunnel 438, according to an embodiment. The wind tunnel 438 includes a test section 400. The test section 400 may include any of the test sections disclosed herein. For example, the test section 400 may include at least one surface 422 defining an enclosed space 402. The test section 400 further includes at least one nozzle (not shown) configured to dispense an agricultural spray 406 into the enclosed space 402. Additionally, the test section 400 includes a stimulus source 408 and a detector 412.

The wind tunnel 438 further includes a blower 440 positioned upstream from the test section 400. The blower 440 may include any suitable device for pushing the air 426 through the test section 400. The blower 440 may be configured to flow the air 426 through the enclosed space 402 at a selected speed. In an embodiment, the selected speed may be less than about 35 miles per hour ("mph"), such as in ranges of about 0 mph to about 5 mph, about 2.5 mph to about 7.5 mph, about 5 mph to about 10 mph, about 7.5 mph to about 12.5 mph, about 10 mph to about 15 mph, about 12.5 mph to about 17.5 mph, about 15 mph to about 20 mph, 17.5 mph to about 22.5 mph, about 20 mph to about 25 mph, about 22.5 mph to about 27.5 mph, about 25 mph to about 30 mph, about 27.5 mph to about 32.5 mph, about 30 mph to about 35 mph, or combinations thereof. Air speeds that are less than about 35 mph may simulate wind conditions that the agricultural spray 406 is exposed to when dispensed from a ground applicator, such as a tractor, truck, an individual carrying the nozzle, etc. However, the blower 440 may be configured to flow the air 426 through the enclosed space 402 at speeds greater than 35 mph, such as greater than 50 mph, greater than 75 miles per hour, or greater than 100 mph. Such high air speeds may simulate wind conditions that the agricultural spray 406 is exposed to when dispensed from an air applicator, such as a helicopter or an airplane.

The wind tunnel 438 may also include a spray particle scrubber 444 positioned downstream from the test section 400. The spray particles scrubber 444 may be configured to collect droplets from the wind tunnel 438 that reach the spray particle scrubber 444 (e.g., spray particles not collected by the recess 424). The spray particle scrubber 444 may prevent the spray droplets from continuing down the wind tunnel 438. With the spray particle scrubber 444, the air 426 may be reused and provided to the blower 440 or the air 426 may be emitted into the environment. In an embodiment, the spray particle scrubber 444 may be configured as a mist extractor. In an embodiment, the spray particle scrubber 444 may be 99.7% effective at removing particles greater than 5 μm diameter. For example, the spray particle scrubber 444 may use angled channels to change the flow path of the particles, allowing them to settle out and run down the channels into a fluid collector (e.g., the recess 424).

In an embodiment, the wind tunnel 438 may include at least one of a first tunnel 442 or a second tunnel 446. The wind tunnel 438 may include the first tunnel 442 when the blower 440 is spaced from the test section 400 and the second tunnel 446 when the spray particle scrubber 444 is spaced from the test section 400. The first tunnel 442 and the second tunnel 446 may couple the blower 440 and the spray particle scrubber 444 to the test section 400 so air may flow from the blower 440 to the test section 400 and from the test section 400 to the spray particle scrubber 444. The first and/or second tunnels 442, 446 may form a straight airflow path or may be at least partially curved.

In an embodiment, at least one of the first or second tunnel 442, 444 may exhibit a cross-sectional shape and cross-section dimension(s) that do not vary along a length thereof. Not varying the cross-sectional shape and the cross-section dimension(s) of at least one of the first or second tunnel 442, 444 may increase the uniformity of the air 426 flowing through the enclosed space 402 (e.g., reduce turbulent air flow). However, in some embodiments, at least one of the first or second tunnel 442, 444 may exhibit a cross-section shape and/or cross-section dimension(s) that vary along at least a portion of the length thereof. For example, the cross-sectional dimension(s) of at least one of the first or second tunnel 442, 444 may vary to modify the speed of the air 426 flowing therein (e.g., decreasing a cross-sectional dimension may increase the speed of the air 426 while increasing a cross-sectional dimension may decrease the speed of the air 426).

In an embodiment, the wind tunnel 438 may include a computer 448. The computer 448 may include a processor, a memory and a network connection. The computer 448 may be communicatively coupled to one or more components of the wind tunnel 438. For example, the computer 448 may be communicably coupled to at least one of the stimulus source 408, the detector 412, the blower 440, the spray particle scrubber 444, the nozzle (not shown), or another component of the wind tunnel. Using the computer 448, an operator may adjust the angle of the agricultural spray 406 relative to the direction of the air 426 flowing through the enclosed space 402 (e.g., change the angle of the agricultural spray 406 relative to the airflow path of the enclosed space 402), cause the stimulus source 408 to emit the stimulus 410, image the agricultural spray 406, flow the air 426 through the enclosed space 402, or another operation of the wind tunnel 438.

It is noted that the wind tunnel 438 is merely an example of a wind tunnel that may, include any of the test sections disclosed herein. Further it is noted that the test sections disclosed herein may be used with any suitable wind tunnel without limitation. For instance, further examples of wind tunnels that may include any of the test sections disclosed herein are disclosed in U.S. Pat. No. 8,689,619 filed on Sep.

13, 2012, U.S. Patent Application Publication No. 2018/0143100 filed on Nov. 2, 107, and ANSI/ASABE 5592.1 published in the American Society of Agricultural and Biological Engineers, the disclosures of each of which is incorporated herein, in its entirety, by this reference.

Figure 5:
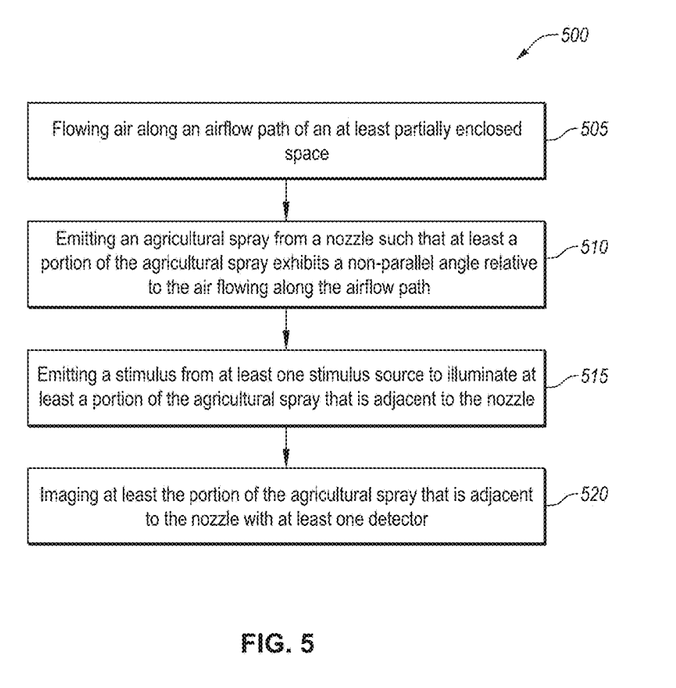
FIG. 5 is a flow chart of an example method 500 of using a wind tunnel including any of the test sections disclosed herein, according to an embodiment.

FIG. 5 is a flow chart of an example method 500 of using a wind tunnel including any of the test sections disclosed herein, according to an embodiment. The method 500 may include one or more operations, functions, or actions as illustrated by one or more blocks 505, 510, 515, or 520. For example, the method 500 may begin with block 505, which recites "flowing air along an airflow path of an at least partially enclosed space." Block 505 may be followed by block 510, which recites "emitting an agricultural spray from a nozzle such that at least a portion of the agricultural spray exhibits a non-parallel angle relative to the air flowing along the airflow path." Block 510 may be followed by block 515, which recites "emitting a stimulus from at least one stimulus source to illuminate at least a portion of the agricultural spray that is adjacent to the nozzle." Block 515 may be followed by block 520, which recites "imaging at least the portion of the agricultural spray that is adjacent to the nozzle with at least one detector."

The blocks included in the described the example method 500 are for illustration purposes. In an example, the blocks may be performed in a different order, eliminated, divided into additional blocks, modified, supplemented with other blocks, or combined into fewer blocks. In an example, the method 500 may include additional unrecited blocks, such as at least partially controlling one or more components of the wind tunnel with a computer.

Block 505 includes "flowing air along an airflow path of an at least partially enclosed space." For example, block 505 may include activating a blower of the wind tunnel so air flows through the test section. In an embodiment, block 505 may include flowing the air through a tunnel extending between the blower and the test section. It is noted that block 505 may include controllably selecting and/or changing the speed of the air flowing along the airflow path.

Block 510 includes "emitting an agricultural spray from a nozzle such that at least a portion of the agricultural spray exhibits a non-parallel angle relative to the air flowing along the airflow path." In other words, block 510 includes emitting the agricultural spray from the nozzle so at least a portion of the agricultural spray exhibits a non-parallel angle relative to the airflow path of the enclosed space. Block 510 may be performed at least one of before, during, or after block 505. For example, if block 510 is performed during block 505, block 510 may include forming droplets via the bag rupture approach to droplet formation.

Block 510 may include controllably selecting and/or adjusting the non-parallel angle between at least a portion of the agricultural spray and the air flowing along the airflow path. For example, block 510 may include manually changing the non-parallel angle or may include changing the angle using an actuator coupled to the nozzle.

Block 515 includes "emitting a stimulus from at least one stimulus source to illuminate at least a portion of the agricultural spray that is adjacent to the nozzle." In an example, block 515 may include emitting visible light or any of the other stimuli disclosed herein towards at least the portion of the agricultural spray that is adjacent to the nozzle. In an example, block 515 may include emitting the stimulus through a transparent section of the at least one surface that defines the enclosed space when the stimulus source is positioned outside of the enclosed space. In an example, block 515 may include adjusting (e.g., focusing, collimating, magnifying, diffusing, etc.) the stimulus using one or more optical elements. In an example, block 515 may include moving the stimulus source manually or using an actuator. In an example, block 515 may be performed at least one of before, during, or after at least one of blocks 505 or 510.

Block 520 includes "imaging at least the portion of the agricultural spray that is adjacent to the nozzle with at least one detector." In an example, block 520 includes imaging at least a portion of the agricultural spray that is adjacent to the nozzle through at least one transparent section of the at least one surface that defines the enclosed space. In an example, block 520 may include adjusting (e.g., focusing, magnifying, diffusing, etc.) the image detected by the detector using one or more optical elements. In an example, block 520 may include moving the detector manually or using an actuator. In an example, block 520 may be performed at least one of before, during, or after at least one of blocks 505, 510, or 515.

The following working examples provide further detail in connection with the specific embodiments described above.

Working Example 1

The agricultural spray of this Working Example 1 was formed by mixing XtendiMAX®, Roundup® PowerMAX®, Class Act® Ridion™, and OnTarget™ together. OnTarget™ is a proprietary drift reduction adjuvant that includes at least one rheology modifier. The product use rates of XtendiMAX® and Roundup® PowerMAX® in the agricultural spray of Working Example 1 were both 22 ounces per acre. The amounts of Class Act® Ridion™ and OnTarget™ in the agricultural spray of Working Example 1 were 1.0 volume % and 0.5 volume %, respectively.

Figure 1C:
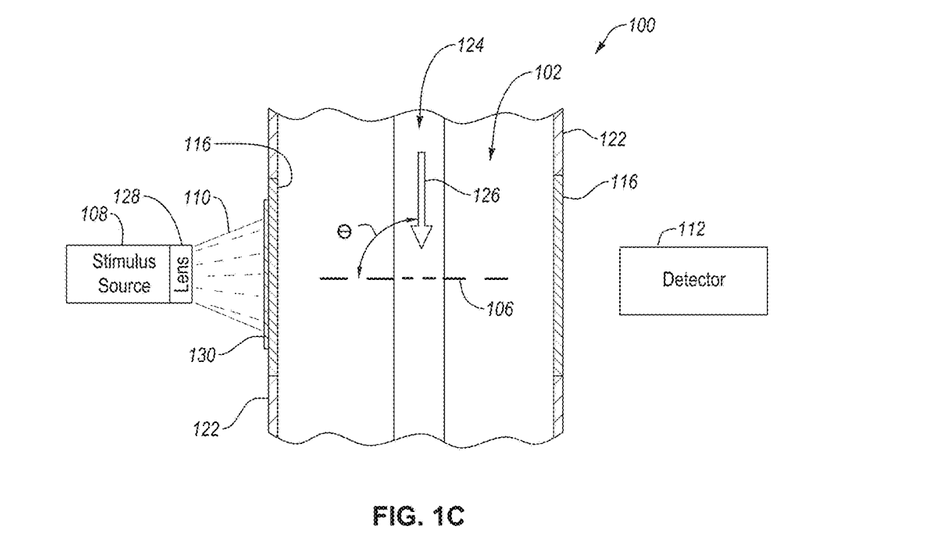
FIG. 1C, which is a top plan view of the test section 100 after the nozzle 104 is selectively repositioned

The test section of the wind tunnel shown in FIGS. 1A-1C was used to test the agricultural spray of Working Example 1. The nozzle of the test section was a Wilger UR 11004. The agricultural spray of Working Example 1 was emitted from the nozzle at 40 pounds per square inch. The air flowing through the test section was held at a constant speed that simulated an ambient air speed of 15 mph and a speed of the applicator of 15 mph. The spray orientation angle θ between air flowing through the test section and the spray sheet was 45°.

Figure 6:
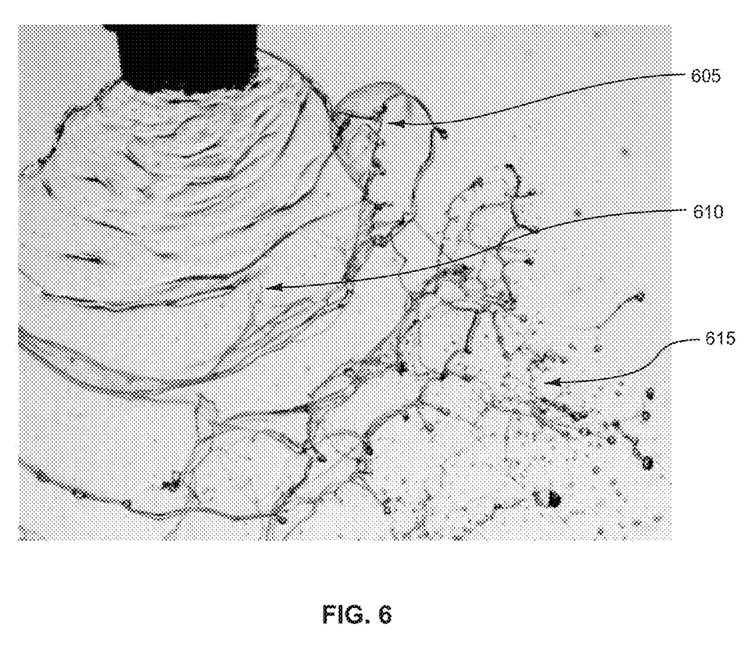
FIG. 6 is an image of the spray sheet of agricultural spray of the Working Example 1 near the nozzle experiencing the bag rupture approach to droplet formation.

FIG. 6 is an image of the spray sheet of agricultural spray of the Working Example 1 near the nozzle experiencing the bag rupture approach to droplet formation. In FIG. 6, a bag is shown that has been formed in the agricultural spray of the Working Example 1 (indicated with arrow 605). FIG. 6 also shows a bag in the process of rupturing (indicated with arrow 610). Droplets formed from a ruptured bag (indicated with arrow 615) is also shown in FIG. 6. In other words, Working Example 1 demonstrates that the test sections disclosed herein may detect when the agricultural spray form droplets according to the bag rupture approach to droplet formation.

Working Example 2

An agricultural spray of the Working Example 1 was provided. InterLock®, a propriety adjuvant that includes at least one perforation-aid type adjuvant, was added to the agricultural spray to form the agricultural spray of Working Example 2. The agricultural spray of Working Example 2 was then sprayed into the test section of the wind tunnel shown in FIGS. 1A-1C using the same method as the agricultural spray of Working Example 1.

Figure 7:
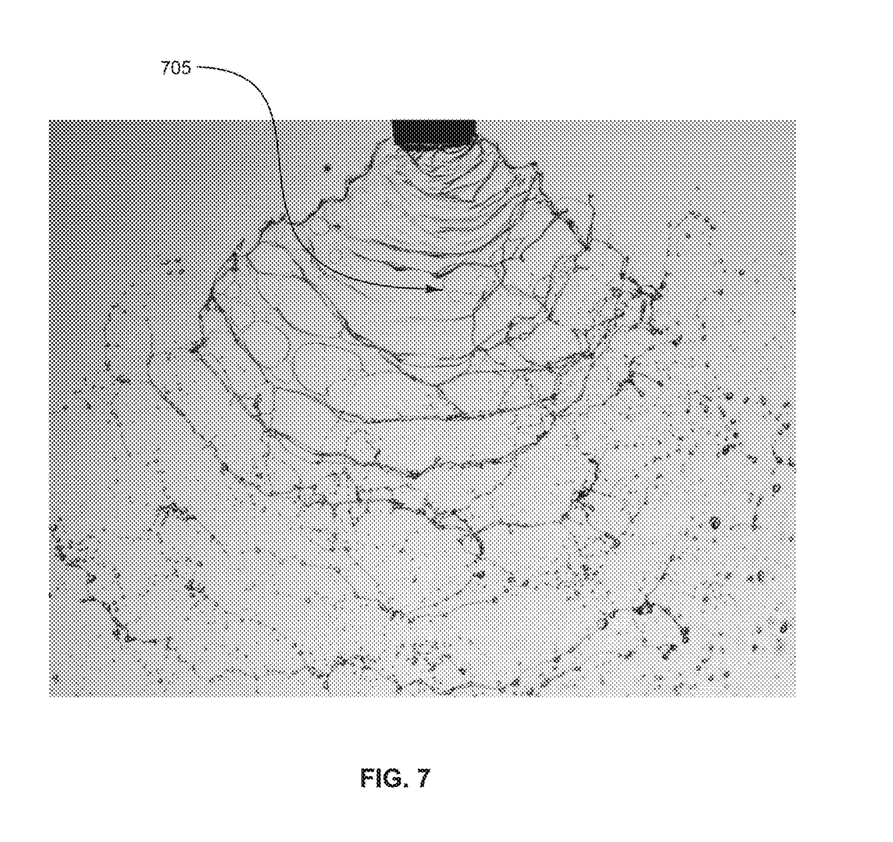
FIG. 7 is an image of the spray sheet of the agricultural spray of Working Example 2 near the nozzle.

FIG. 7 is an image of the spray sheet of the agricultural spray of Working Example 2 near the nozzle. FIG. 7 illustrates that the agricultural spray of Working Example 2 exhibited little to no bag formation. Instead, FIG. 7 illustrates that the spray sheet formed from the agricultural spray of Working Example 2 formed perforations (indicated with arrow 705) instead of bags. In other words, Working Example 2 demonstrates that the test sections disclosed herein may detect when the agricultural spray does not form droplets according to the bag rupture approach to droplet formation.

We claim:

1. A test section, comprising:
   at least one surface defining an at least partially enclosed space, the at least partially enclosed space defining an airflow path for air to flow;
   a nozzle disposed in the at least partially enclosed space, the nozzle configured to spray an agricultural spray, the nozzle positioned to emit the agricultural spray such that at least a section of the agricultural spray exhibits a non-parallel angle relative to the airflow path defined by the at least partially enclosed space;
   at least one stimulus source positioned to illuminate at least a portion of the agricultural spray adjacent to the nozzle, wherein the portion of the agricultural spray includes a region of the agricultural spray initially exiting the nozzle that forms a continuous sheet-like portion defining an initial spray pattern; and
   at least one detector positioned to image at least the portion of the agricultural spray adjacent to the nozzle.

2. The test section of claim 1, wherein the at least one surface comprises a top surface, a bottom surface, and two lateral surfaces extending between the top surface and the bottom surface.

3. The test section of claim 1, wherein the at least one surface comprises a first transparent section and a second transparent section, the at least one stimulus source positioned to emit the stimulus into the at least partially enclosed space through the first transparent section, the at least one detector positioned to image at least the portion of the agricultural spray that is adjacent to the nozzle through the second transparent section.

4. The test section of claim 1, wherein the at least partially enclosed space is a completely enclosed space.

5. The test section of claim 1, wherein the nozzle comprises a flat fan nozzle and an entirety of the agricultural spray exhibits the non-parallel angle relative to the airflow path defined by the at least partially enclosed space.

6. The test section of claim 5, wherein the non-parallel angle is generally perpendicular to the airflow path defined by the at least partially enclosed space.

7. The test section of claim 1, wherein the nozzle comprises a hollow fan nozzle.

8. The test section of claim 1, wherein the nozzle is positioned to emit the agricultural spray in a direction that is substantially parallel to gravity.

9. The test section of claim 1, wherein the at least one stimulus source comprises a pulsed stimulus source.

10. The test section of claim 1, wherein the at least one stimulus source comprises a pulsed laser disposed outside of the at least partially enclosed space; and
    further comprising at least one of an aspheric lens, a positive or negative spherical lens, or combination of positive and negative concaved cylindrical lenses disposed outside of the at least partially enclosed space between the pulsed laser and the at least one surface.

11. The test section of claim 1, wherein the at least one stimulus source comprises a continuous light source.

12. The test section of claim 1, wherein the at least one stimulus source comprises a collimated light source.

13. The test section of claim 1, wherein the at least one detector is positioned such that an imaging plane detected by the at least one detector is generally perpendicular to the portion of the agricultural spray.

14. The test section of claim 1, wherein the at least one detector is positioned such that an imaging plane detected by the at least one detector is generally parallel to the portion of the agricultural spray.

15. The test section of claim 1, further comprising one or more lenses configured to collimate the stimulus emitted from the at least one stimulus source.

16. The test section of claim 1, further comprising a collection or condenser lens and an aperture, wherein the collection or condenser lens and the aperture are positioned and configured to improve a resolution of the image detected by the at least one detector.

17. The test section of claim 1, further comprising one or more lenses positioned and configured to magnify the image detected by the at least one detector.

18. A wind tunnel, comprising:
    a test section comprising:
        at least one surface defining an at least partially enclosed space, the at least partially enclosed space defining an airflow path for air to flow;
        a nozzle disposed in the at least partially enclosed space, the nozzle configured to spray an agricultural spray, the nozzle positioned to emit the agricultural spray such that at least a section of the agricultural spray exhibits a non-parallel angle relative to the airflow path defined by the at least partially enclosed space;
        at least one stimulus source positioned to illuminate at least a portion of the agricultural spray adjacent to the nozzle, wherein the portion of the agricultural spray includes a region of the agricultural spray initially exiting the nozzle that forms a continuous sheet-like portion defining an initial spray pattern; and
        at least one detector positioned to image the portion of the agricultural spray adjacent to the nozzle; and
    a blower configured to provide the air to the test region.

19. The wind tunnel of claim 18, wherein the at least partially enclosed space is a completely enclosed space.

20. A method, comprising:
    flowing air along an airflow path of an at least partially enclosed space, the at least partially enclosed space defined by at least one surface;
    emitting an agricultural spray from a nozzle such that at least a section of the agricultural spray exhibits a non-parallel angle relative to the air flowing along the airflow path;
    emitting a stimulus from at least one stimulus source to illuminate at least a portion of the agricultural spray that is adjacent to the nozzle, wherein the portion of the agricultural spray includes a region of the agricultural spray initially exiting the nozzle that forms a continuous sheet-like portion defining an initial spray pattern; and
    imaging at least the portion of the agricultural spray that is adjacent to the nozzle with at least one detector.

* * * * *